United States Patent [19]
Corbo

[11] Patent Number: 4,854,300
[45] Date of Patent: Aug. 8, 1989

[54] DISCARDABLE ADJUSTABLE VAGINAL SPECULUM

[76] Inventor: Antonino Corbo, Av. La Plata 1460, 2nd Floor, (1250) Buenos Aires, Argentina

[21] Appl. No.: 173,467

[22] Filed: Mar. 25, 1988

[30] Foreign Application Priority Data

Mar. 26, 1987 [AR] Argentina .............................. 307124

[51] Int. Cl.$^4$ ............................................... A61B 1/30
[52] U.S. Cl. .......................................... 128/3; 128/17; 128/20
[58] Field of Search .......................... 128/3, 17, 18, 20; 604/111, 306

[56] References Cited
U.S. PATENT DOCUMENTS 4,667,837  5/1987  Vitello et al. .................... 604/111 X

FOREIGN PATENT DOCUMENTS 1462929  1/1977  United Kingdom .................. 128/17

Primary Examiner—William H. Grieb
Attorney, Agent, or Firm—Fleit, Jacobson, Cohn, Price, Holman & Stern

[57] ABSTRACT

The invention comprises a low-cost vaginal speculum made of plastics for vaginal observation and minor operations, particularly apt for routine examination and periodical check-ups. In order to provide a safeguard against reuse of the speculum and guarantee non-use to the patient, the observation window of the instrument is initially provided with a patch sealably closing it. The patch may be removed in sight of the patient by breaking off a pair of tabs, after which it may not be replaced; thus the speculum has to be discarded after first use. The speculum is further provided with means for regulating the opening of its tongs to reduce the possibility of hurting or frightening the patient. In a preferred embodiment, the means for adjusting the opening of the tongs comprise two pivoted lever-arms which cam on the inside surfaces of the respective tongs. Each lever arm extends through a slot in a wall of the speculum to form an actuator head accessible to the doctor. At its opposite end, each lever-arm comprises a notched end caming on the inside of the respective tong, preferably against a guide-ratch.

10 Claims, 2 Drawing Sheets

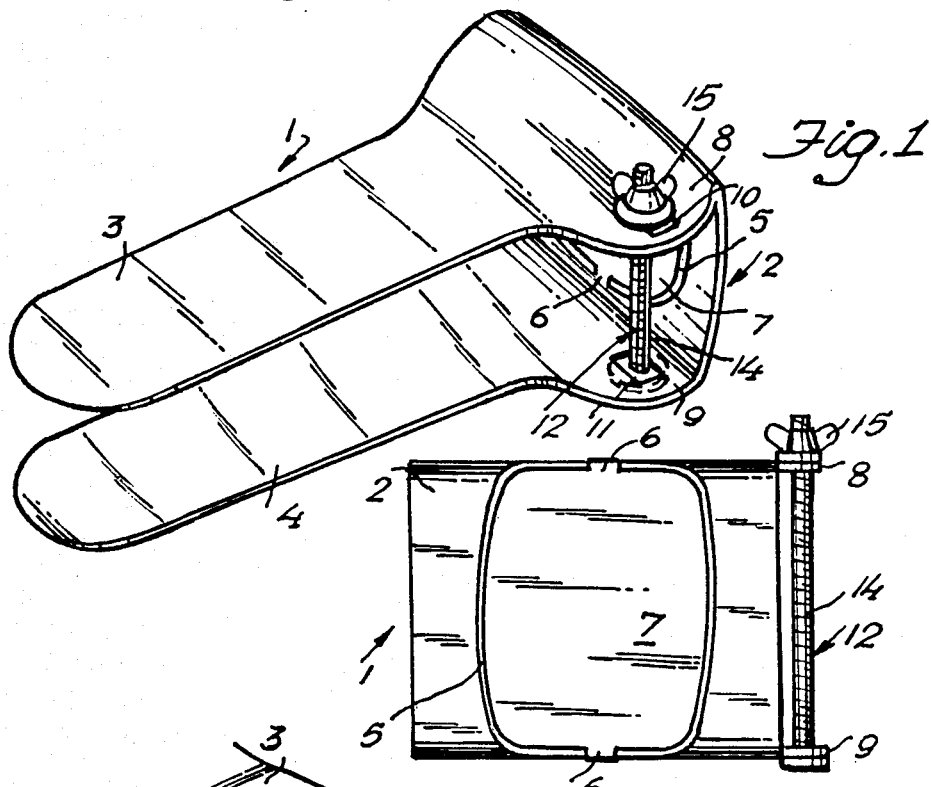
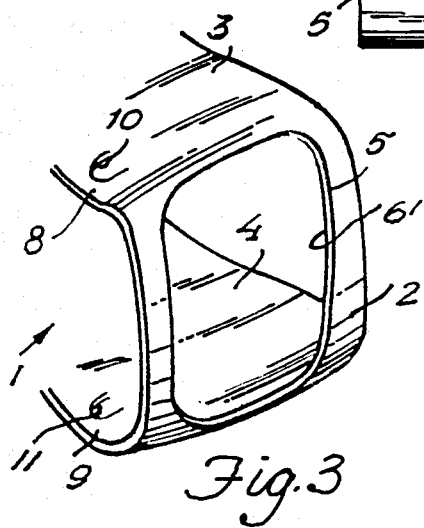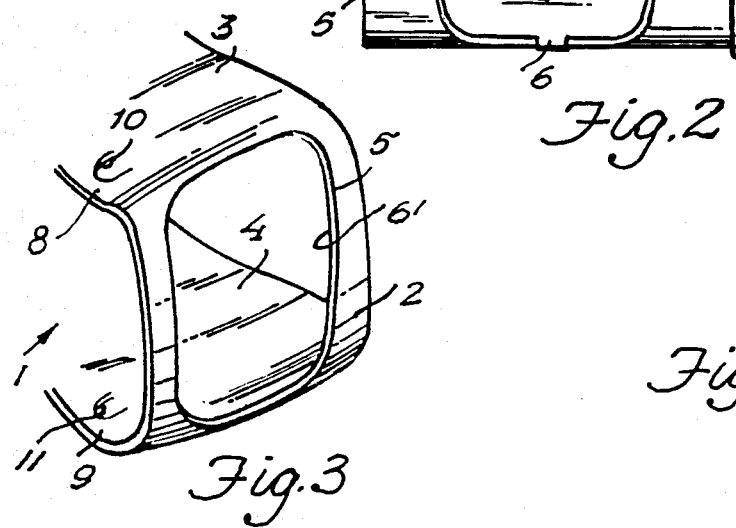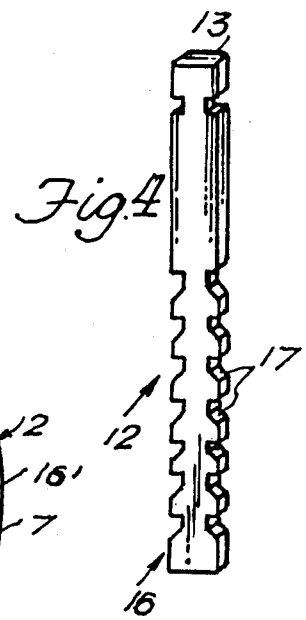
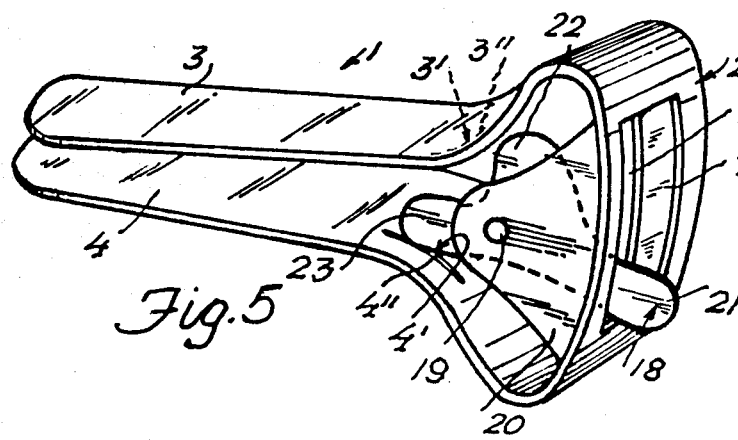

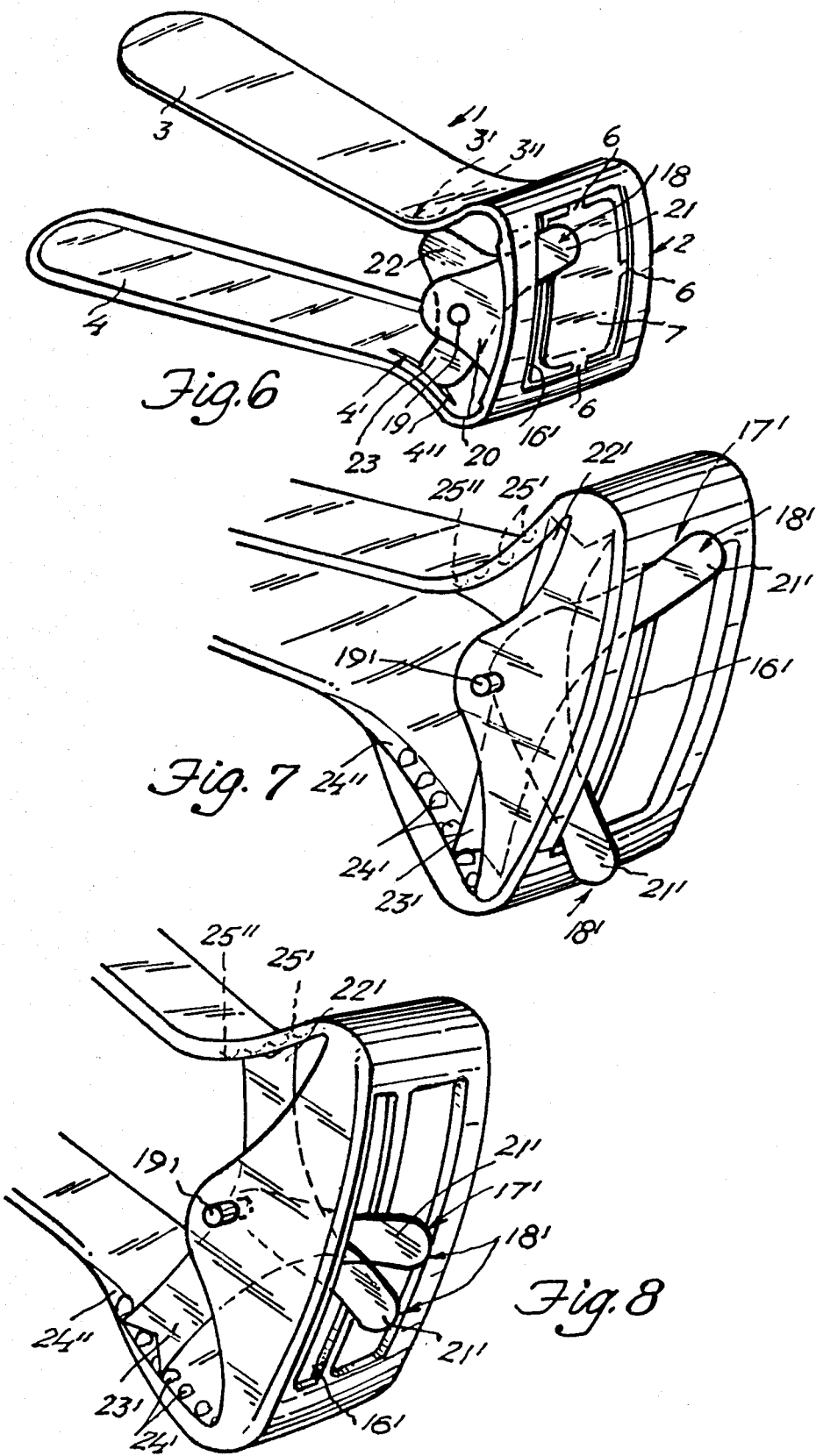

DISCARDABLE ADJUSTABLE VAGINAL SPECULUM

FIELD OF THE INVENTION

The present invention refers to a separating means having use in gynecological medicine and more specifically to a discardable and adjustable vaginal speculum providing important advantages in both its strictly structural and functional features with regard to known specula.

The instrument of the present invention is generally destined for routine examinations and periodical checkups, for instance, for obtaining Papanicolau or flux samples, cholposcopy, and other vaginal examinations wherein the survey area must be conveniently exposed. In general, it is adapted for use in the field of preventive medicine, and in largely populated areas in particular.

PRIOR ART

Vaginal specula are widely known in medicine and have been in use for some time for gynecological observations and minor operations, however their design and structure features still cause a series of psychological drawbacks to patients.

The traditional speculum was made of metal, usually stainless steel, such that it could be reused after being properly sterilized. However, its metallic nature resulted in that the temperature thereof was appreciably less than the internal temperature of the human body, thus causing a very unpleasant physical sensation when it was inserted therein. This unpleasantness was in addition to the psychological impact which resulted from its very use in such a sensitive area, in addition to the uneasiness and distrust over the possible lack of hygiene forthcoming from medical instruments which may seem to have been pre-used.

A further disadvantage is that the manipulation of these specula is hindered by the lack of precise means for adjusting the size of the opening.

Also known in the art is a presterilized, discardable speculum developed by Mr. Hugo Leibovich (Argentine Pat. No. 228,414). These specula are low-cost instruments made of plastics which by virtue of its physical properties are self-expandable, hence avoiding some of the previously mentioned drawbacks. For instance, before use, the instrument is normally in a widely open or unfolded configuration, the size of which is enough to cause an unfavourable psychological impression. The patient's uncertainty regarding previous non-use of the instrument also incides negatively in her mind.

Re-use of the speculum is particularly ill-advisable since the material of the instrument comprises an internal lattice system of little cells and capillary elements which absorb secretions impossible to eliminate afterwards with antiseptics. Furthermore, reuse would convert the speculum in a vehicle for transmitting contagious infections.

SUMMARY OF THE INVENTION

The present invention provides a novel vaginal speculum which overcomes all the aforementioned drawbacks and disadvantages. In the first place, the speculum of the present invention is of the discardable type and is provided with a device guaranteeing absolute certainty that the instrument has not been previously used. This guarantee device is a simple, non-replaceable seal means devised so that the patient may see for herself that the instrument could not have been used previously on another patient, whereafter the seal may be broken in front of her to be ready for use. In the second place, the present invention concerns a vaginal speculum which may be provided in an initially closed position and having a manual device for easily adjusting the size of the opening, so as to reduce the chances of hurting or frightening the patient. The adjusting device includes retainer means for holding the tongs in selective angular positions. These and other salient features of the present invention will become more evident in the course of the description hereinafter aided by the accompanying drawings.

BRIEF DESCRIPTION OF THE DRAWINGS

FIG. 1 is a general view in perspective of the speculum of the present invention.

FIG. 2 is an end view of the speculum of FIG. 1, showing the safety patch of an unused instrument.

FIG. 3 is the same end view of FIG. 2, wherein the safety patch has however been broken for use.

FIG. 4 is a view of a device for adjusting the opening of the separator tongs of the speculum of the present invention.

FIGS. 5 and 6 illustrate an alternative embodiment of the means for adjusting the opening of the speculum tongs.

FIGS. 7 and 8 show a further alternative means for adjusting the opening of the separator tongs.

In the different drawings, like reference numbers are used to indicate the same or corresponding parts.

DETAILED DESCRIPTION OF THE DRAWINGS

The speculum indicated by reference numeral 1 in the drawings comprises a flat cross-wall 2 from which two rigid and elongated separator tongs 3, 4 extend facing each other. As is traditional, the section of each of the tongs 3, 4 is concave-convex, adopting a shape corresponding to the anatomy of the vaginal cavity.

Said wall 2 features a generally square window 5 with rounded edges. The window 5 is interrupted at two points of its extension by brittle tabs 6 which initially hold in place a central opaque patch 7 in the form of a safety seal.

Each one of the aforementioned tongs 3, 4 may be larger at its end adjacent the wall 2, so as to define respective ears 8, 9. Each of the ears 8, 9 is perforated right through by a respective orifice 10, 11, in a way in which the orifices 10, 11 are aligned with each other and retain a means for regulating or adjusting the size of the opening of the speculum.

The adjusting means 12 may be embodied in various practical forms, such as the one illustrated in FIGS. 1 and 2 consisting of a threaded rod 14 operated by means of a counter-pressure butterfly nut 15. The butterfly nut 15 may be screwed in or out so as to reduce or increase the distance between the tongs 3, 4 which push away from each other by virtue of the elastic memory which is a property of the plastics material with which the specula are manufactured. A different embodiment is illustrated in FIG. 4, wherein the adjusting means 12 is formed by a flat peg 16 having marginal grooves or notches 17 adapted to latch into the orifices 10, 11 when the finger head 13 is twirled a quarter-turn. The gynecologist uses the flat peg 16 to adjust the opening of the speculum 1 by lifting or lowering one of the tongs 3, 4 until one of the notches 17 latches into the corresponding orifice 10, 11.

The operation of the speculum 1 of the present invention should be easy to imagine from what is illustrated and the foregoing. In order for it to be usable, the brittle tabs 6 must be broken off so that the central path 7 may be torn off to define a wide window 6' through which observations may be made and instruments passed through, as may be understood from FIG. 3.

In this manner, any doubt regarding the single-use of each instrument is done away with, since the patient may see for herself how the doctor breaks the tabs 6 in front of her before proceeding to use the instrument. Since both visual and physical access is virtually impossible if not through the window 6', the unbroken patch 7 is in itself a warrant that the speculum 1 has not being previously used.

As is traditional, the free ends of the tongs 3, 4 are closed and inserted in the vagina of the patient; after which the doctor may easily act on the regulating means 13, 15 to gradually separate these tongs 3, 4 from each other until the field of observation through the window 6' is wide enough.

Once the examination and the operation have been finished through this window 6', the speculum 1 must be discarded, since the patch 7 cannot be replaced once it has been torn off the body of the instrument 1, thereby guaranteeing an effective safety seal as previously mentioned.

FIGS. 5 and 6 refer to yet another embodiment of the adjustable and self-retaining opening device of the invention. The instrument 1 includes a control lever 18 which is mounted to pivot on a fulcrum or pin 19 located on an ear 20 extending inwards from the wall 2. The lever arm 18 extends through a slot 26 in the wall 2 to form an actuator end 21. In order to enable optimum use of the wall area 2 for the window opening 6', the slot 26 is arranged near one edge of the wall 2 alongside the window 6'.

On the opposite, active end thereof, the lever 18 includes a pair of adjacent crests or lobules 22, 23 which push against the internal sides of said tongs 3, 4 in the form of push-cams.

In this way it can be seen that by turning the lever 18 at the actuator-end 21 about its fulcrum 19, the lobules 22, 23 will be moved and pushed against the inside of the tongs 3, 4 to gradually carry them to a position of maximum opening, passing through a full range of intermediate-size openings.

To help in opening, it is convenient to provide these tongs 3, 4 with internal guides 3', 4' which may be formed by simple ruts 3'', 4'' in which the edges of the lobules 22, 23 may partially fit in, thus impeding unsuitable lateral displacements. Of course, the guide-ruts may be replaced in practice by guider ribs or any other equivalent means.

A preferred embodiment of the present invention is shown in FIGS. 7 and 8 which functions according to the same principles, and meets the same objects in relation to the foregoing. A device 17' carries out the opening adjusting or regulating function of the lever 18', similarly pivoting about the fulcrum pin 19'. However, as illustrated, this control device 17' now comprises two actuator arms 21'. Practically the only difference, rather structural than conceptual, is that the lobules 22, 23 are substituted by active push-cam ends 22', 23' provided on the levers 18'. In this way, each lever piece 18' has a V-like shape which makes it relatively easy to manufacture.

As before, the operative ends 21' emerge through the slot 16' such that mutual advancing of the arms 18' towards each other will produce an angular scissor movement around the fulcrum 19'. Consequently, the active end 22' will push against one of the tongs 3 of the speculum 1 whilst the active end 23' will do likewise against the other tong 4, and the degree of opening or separation of the tongs 3, 4 will depend on the angular position of the arms 18'.

Furthermore, the guides on the insides of the tongs 3, 4 are ratched with teeth 24', 25', such that during the above described movement, the opposite active ends 22', 23' of the "V"-shaped levers 18' will jump from one tooth 24', 25' to the next, eventually stopping against end-stubs 24'', 25'' which limit the separation between the tongs 3, 4 to a maximum. The intermediate teeth 24', 25' serve to retain the tongs 3, 4 in a given angle selected by the acting gynecologist. To this end, the cam ends of the lever arms are provided with means 23' for engaging the teeth 24', 25' in the form of a pointed end or a "V"-shaped notch (as illustrated).

Finally, in order to help the doctor with his task of visualizing the field of observation and/or operation, the inside face of the cross-wall 2 of the speculum 1 may hold a small lamp fixture. This may help to shorten the operation time and thereby relieve the patient of most of her dramatic experience.

Although the essential features of the invention have been brought out by means of preferred embodiments, the invention is not limited to these embodiments and extends on the contrary to all alternative forms within the purview of the appended claims.

I claim:

1. A vaginal speculum comprising two separator tongs, a transversal wall from which said tongs extend facing each other, said wall having a window therein adapted for observation and passage of instruments, and means for initially closing said window, said means comprising a safety seal which once removed may not be replaced thereby providing evidence of prior use of the speculum.

2. A vaginal speculum as claimed in claim 1, characterized in that said seal comprises an opaque patch affixed to the wall of the speculum by means of at least two brittle tabs.

3. A vaginal speculum as claimed in claim 1, characterized by further comprising means for regulating and adjusting the separation between said tongs and for retaining said tongs in a selected angular position.

4. A vaginal speculum as claimed in claim 3, characterized in that said regulating and adjusting means comprises a threaded rod on which a butterfly nut may be operated for adjusting the separation between said tongs, each one of said tongs including ears provided with orifices for said rod.

5. A vaginal speculum as claimed in claim 3, characterized in that said regulating and adjusting means comprises a flat peg provided with marginal notches on each of each two opposite edges and a handling head at a free end thereof, said peg being inserted in respective orifices provided in each ear of a pair of ears which project sideways from each one of said tongs.

6. A vaginal speculum as claimed in claim 3, characterized in that said regulating and adjusting means comprises control lever means pivoted on the body of the speculum, said lever means passing through said wall and terminating in at least one actuator arm, and said lever means including cam means for pushing on the inside of said tongs.

7. A vaginal speculum as claimed in claim 6, characterized in that said control lever means comprises a single arm and two push-cams, each push-cam comprising a respective lobule projecting from and integrated with said single arm.

8. A vaginal speculum as claimed in claim 6, characterized in that said control lever means comprises two arms pivoted on each other and the body of the speculum in the form of scissors, each arm having one end projecting outside said wall for actuation and an opposite end forming a cam pushing on the inside of a respective tong.

9. A vaginal speculum as claimed in claim 6, characterized by said cam means including retainer means engaging a series of teeth ratching a guide on the inside one of said tongs.

10. A vaginal speculum as claimed in claim 6, characterized by said lever means passing through a narrow slot in said wall, which slot is located alongside an observation and operation window.

* * * * *